United States Patent

Nita

[11] Patent Number: 5,827,203
[45] Date of Patent: Oct. 27, 1998

[54] ULTRASOUND SYSTEM AND METHOD FOR MYOCARDIAL REVASCULARIZATION

[76] Inventor: Henry Nita, 26051 Malaga La., Mission Viejo, Calif. 92692

[21] Appl. No.: 840,972

[22] Filed: Apr. 21, 1997

[51] Int. Cl.⁶ .................................................. A61B 17/22
[52] U.S. Cl. ................................................ 601/2; 604/22
[58] Field of Search ............................ 601/2, 4; 604/22; 606/128, 169, 170; 600/439

[56] References Cited

U.S. PATENT DOCUMENTS

| | | | |
|---|---|---|---|
| 4,016,882 | 4/1977 | Broadwin et al. | 128/305 |
| 4,136,700 | 1/1979 | Broadwin et al. | 128/305 |
| 4,827,911 | 5/1989 | Broadwin et al. | 128/305 |
| 4,931,047 | 6/1990 | Broadwin et al. | 604/22 |
| 5,000,185 | 3/1991 | Yock | 600/459 |
| 5,015,227 | 5/1991 | Broadwin et al. | 604/22 |
| 5,267,954 | 12/1993 | Nita . | |
| 5,269,291 | 12/1993 | Carter | 601/2 |
| 5,304,115 | 4/1994 | Pflueger et al. . | |
| 5,318,014 | 6/1994 | Carter . | |
| 5,380,316 | 1/1995 | Aita et al. . | |
| 5,389,096 | 2/1995 | Aita et al. . | |
| 5,431,663 | 7/1995 | Carter . | |
| 5,607,421 | 3/1997 | Jeevanandam et al. | 606/15 |

Primary Examiner—Brian Casler
Attorney, Agent, or Firm—Raymond Sun

[57] ABSTRACT

Methods of improving the circulation of blood to the muscle of the heart of a patient are disclosed. In a first method, a guidable elongated flexible ultrasound device is inserted into a patient's vasculature, and its distal end guided to an area of interest within the patient's heart to which increased blood flow is desired, where ultrasonic energy is applied to the area of interest via the distal end. In a second method, a distal end of an ultrasound device is directed into a patient's chest cavity, and guided within the patient's chest cavity to engage an exterior area of interest of the patient's heart to which increased blood flow is desired, where ultrasonic energy is applied to the area of interest via the distal end.

22 Claims, 6 Drawing Sheets

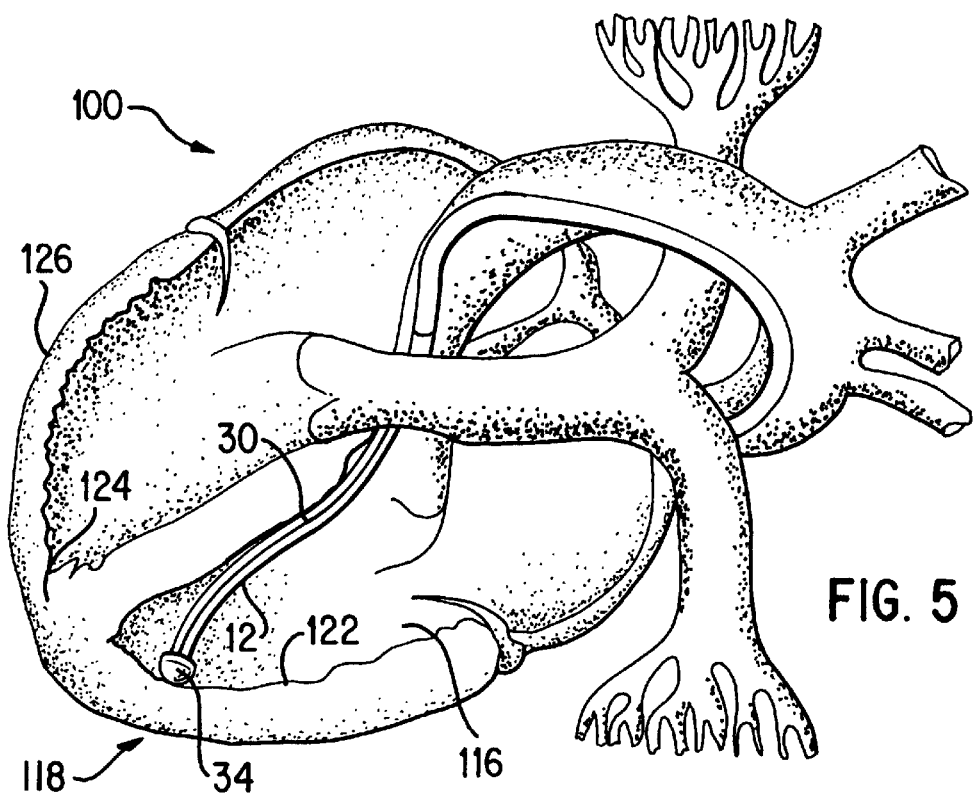
FIG. 5
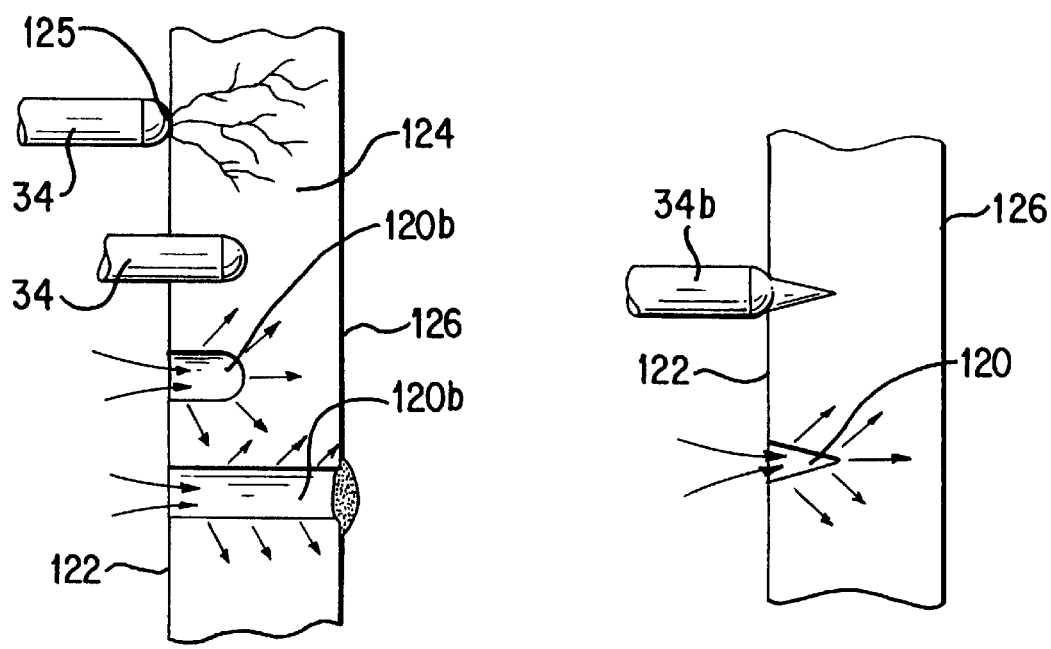
FIG. 6A
FIG. 6B

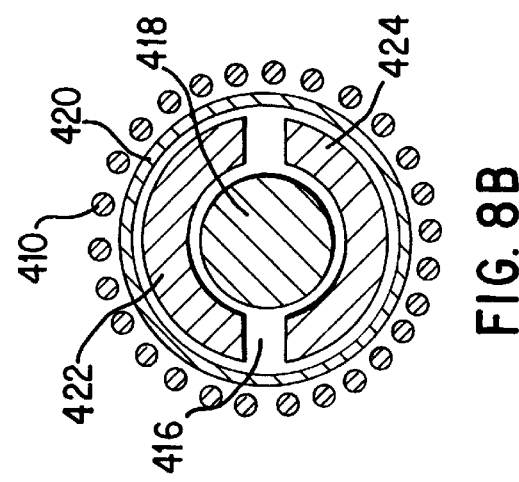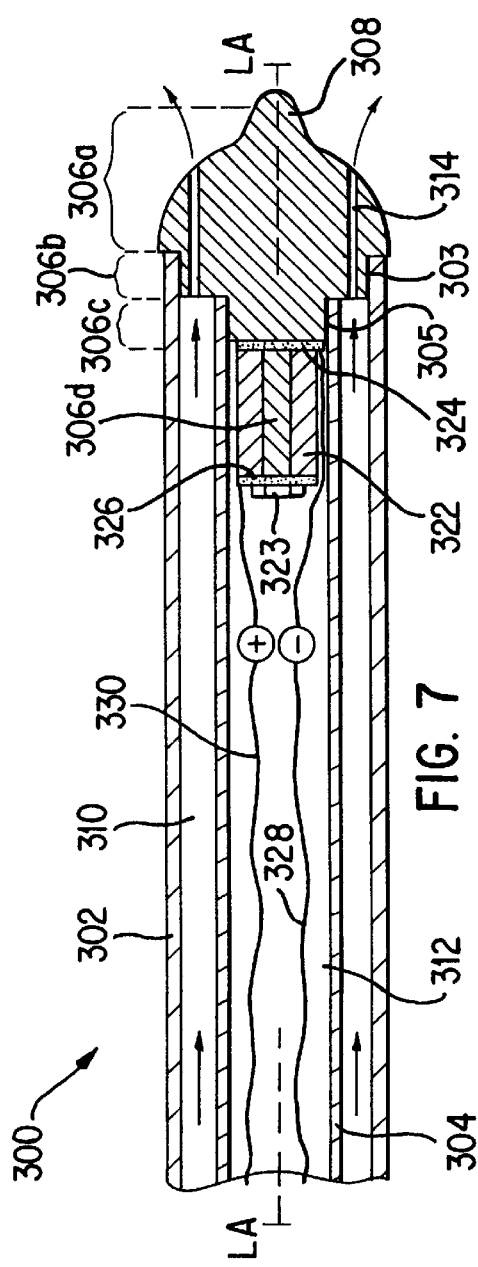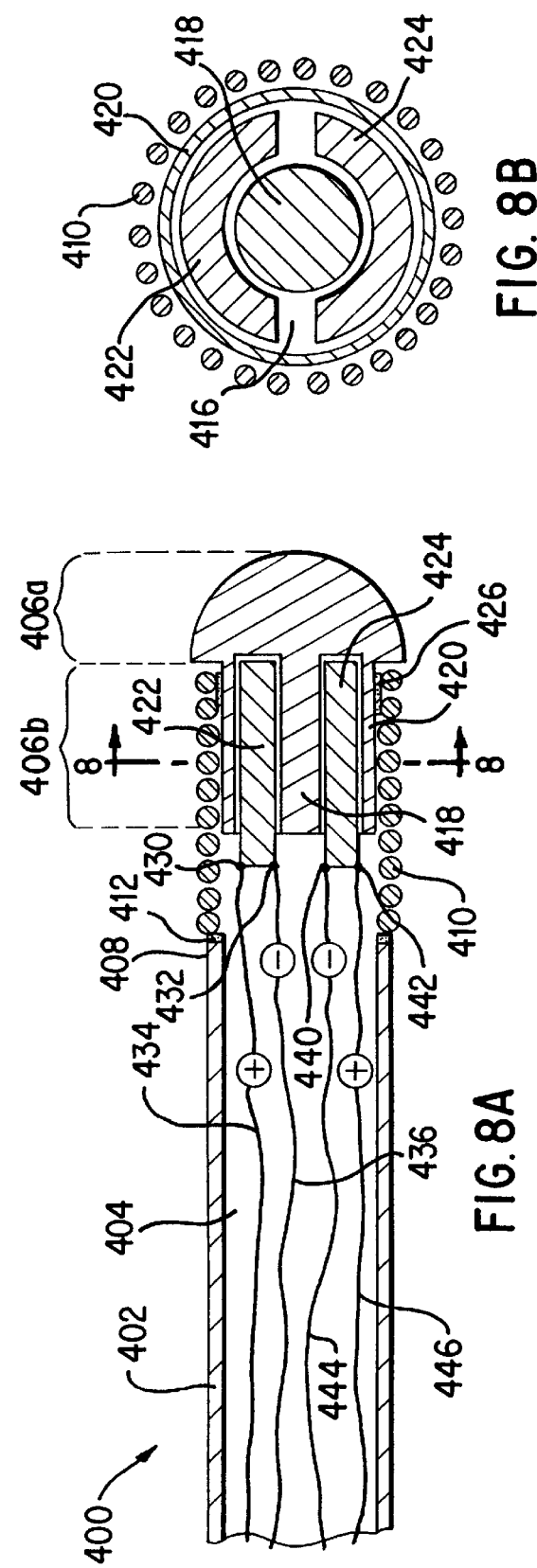

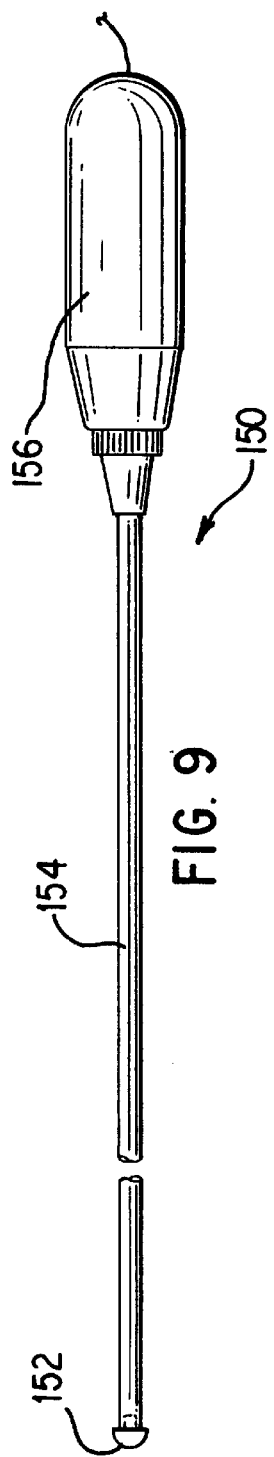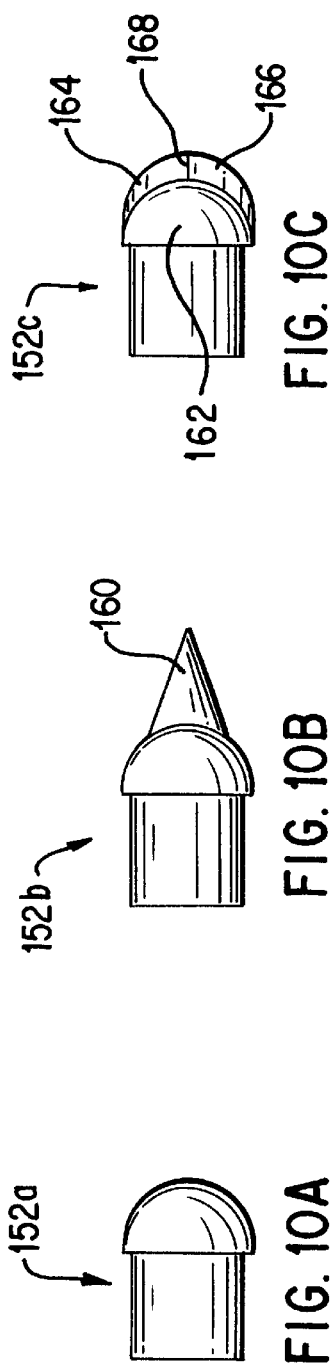

ULTRASOUND SYSTEM AND METHOD FOR MYOCARDIAL REVASCULARIZATION

BACKGROUND OF THE INVENTION

1. Field of the Invention

The present invention relates to systems and methods for use in improving the flow of blood to the heart muscle, and in particular, to the use of ultrasound systems and methods for myocardial revascularization.

2. Description of the Prior Art

A large variety of medical devices and methods have been introduced for treating cardiovascular disease. Alternatives to open heart surgery and cardiovascular bypass surgery are continually being sought to treat cardiovascular disease. Many non-surgical procedures have been developed and used for treating certain conditions, such as PTCA (percutaneous transluminal coronary angioplasty), laser angioplasty, and atherectomy, which are directed to reducing stenosis within a vessel. However, there are still certain cardiovascular conditions that require bypass or other invasive surgery.

Myocardial revascularization is a procedure that has traditionally been treated by bypass surgery. Myocardial revascularization is needed when the coronary arteries that deliver the heart's own blood supply become clogged, causing the muscle wall of the heart to be starved of oxygen and creating painful angina.

One method for treating this condition is known as laser myocardial revascularization (LMR). In LMR, channels are formed in the heart wall from the outer wall (i.e., the epicardium) through the inner wall (i.e., the endocardium) using a $CO_2$ laser, to provide blood flow to ischemic heart muscle. This procedure follows a surgical cutdown. External pressure placed on the outer wall to promote clotting is used to stop bleeding from the interior of the heart to the outside. However, LMR procedures still require that a patient's chest wall be opened in order to access the heart muscle with the laser devices. Thus, this procedure requires major surgery that is highly invasive.

Alternatives to bypass surgery have been developed for myocardial revascularization. One such non-invasive alternative is described in U.S. Pat. No. 5,554,152 to Aita et al. ("the '152 patent"). The '152 patent describes a method for intra-operative myocardial revascularization that includes inserting a portion of an elongated flexible lasing apparatus into the chest cavity of a patient, and lasing channels from the epicardium through the myocardium of the heart. The lasing apparatus is guided to an area exterior to a ventricle of a patient's heart, and the distal end of the apparatus is directed to an area of interest where the epicardium is irradiated with laser energy to form a channel from the epicardium through the myocardium and the endocardium. An exterior portion of the channel is then sealed.

Another such non-invasive alternative is described in U.S. Pat. No. 5,389,096 to Aita et al. ("the '096 patent"). The '096 patent describes a method for percutaneous myocardial revascularization that includes inserting a deflectable elongated flexible lasing apparatus into the vasculature of a patient, generally through one of the major vessels affording access to the interior of the heart. The apparatus is then guided into the interior of the heart, and the distal end of the apparatus is directed to an area of interest where the endocardium is irradiated with laser energy to form a channel through the myocardium for a desired distance. The channels may be formed without perforating the epicardium of the heart.

The methods described in the '152 and '096 patents require the use of laser energy, which may sometimes be ineffective due to mechanical thermal damage or necrosis, which kills healthy cells. Laser energy also kills nerves, thereby temporarily relieving angina, but it permanently damages the heart muscle, and it has not been proven over the long term that heart blood perfusion has actually been improved. Laser systems for providing the laser energy can also be expensive.

Thus, there remains a need for alternative minimally invasive devices and procedures for effecting myocardial revascularization.

SUMMARY OF THE DISCLOSURE

In order to accomplish the objects of the present invention, there is provided a first method of improving the circulation of blood to the muscle of the heart of a patient, comprising the steps of inserting a guidable elongated flexible ultrasound device into a patient's vasculature, then guiding a distal end of the ultrasound device to an area of interest within the patient's heart to which increased blood flow is desired, and then applying ultrasonic energy to the area of interest.

In one embodiment according to the first method of the present invention, the step of applying ultrasonic energy further includes massaging the area of interest without cutting or removing any tissue of the heart wall at the area of interest. This may be followed by removing or cutting some tissue from the area of interest. This may further be followed by forming a channel in the heart wall at the area of interest without perforating the epicardium of the heart wall at the area of interest. This may further be followed by forming a channel in the heart wall at the area of interest through the epicardium.

In one embodiment, the first method according to the present invention applies ultrasonic energy between heart beats. The ultrasound device may be introduced into a patient's vasculature by guiding it through a deflectable guiding catheter, or by passing the ultrasound device over a guidewire that has been positioned at the area of interest.

The ultrasound device used with the first method of the present invention may be provided with an endoscopic visualization apparatus for visualizing the area of interest.

The ultrasound device may be provided with a blunt distal head, or a sharp edge, at its distal end. The ultrasound device used with the first method of the present invention may also be provided with a transducer adjacent its distal end. The transducer may be used to generate longitudinal vibrations, or to generate radial vibrations which create energy, at the distal end of the ultrasound device.

The present invention provides a second method of improving the circulation of blood to the muscle of the heart of a patient, which comprises the steps of directing a distal end of an ultrasound device into a patient's chest cavity, then guiding the distal end of the ultrasound device within the patient's chest cavity to engage an exterior area of interest of the patient's heart to which increased blood flow is desired, and then applying ultrasonic energy to the area of interest.

In one embodiment according to the second method of the present invention, the step of applying ultrasonic energy further includes massaging the area of interest without cutting or removing any tissue from the exterior of the heart at the area of interest. This may be followed by forming a channel in the heart wall at the area of interest. The second method according to the present invention applies ultrasonic energy between heart beats.

Thus, the present invention provides ultrasound devices and methods that can be used to revascularize the myocardium using minimally-invasive procedures. The present invention minimizes injury to the heart wall by providing the physician with the option of not cutting or removing any tissue from the wall of the heart if massaging of the heart tissue is sufficient to revascularize the myocardium. The ultrasound devices according to the present invention further provide the physician with the option of forming channels of different depths and sizes, thereby allowing the physician to adapt the procedure to different cardiovascular conditions. In addition, ultrasonic energy is less traumatic than laser energy.

BRIEF DESCRIPTION OF THE DRAWINGS

FIG. 5 is a schematic section of a human heart showing percutaneous revascularization of the myocardium according to the present invention;

FIGS. 6A and 6B are schematic sectional views of channels created by percutaneous revascularization of the myocardium according to the present invention;

FIG. 7 is a longitudinal cross-sectional view of another ultrasound device according to the present invention for use in effecting percutaneous revascularization of the myocardium;

FIG. 8A is a longitudinal cross-sectional view of a further ultrasound device according to the present invention for use in effecting percutaneous revascularization of the myocardium;

FIG. 8B is a cross-sectional view through line 8—8 of FIG. 8A;

FIG. 9 is a partial enlarged perspective view of an ultrasound device according to the present invention for use in effecting intra-operative revascularization of the myocardium;

FIGS. 10A to 10E are partial enlarged perspective views of distal tips that may be used in connection with the ultrasound device of FIG. 9;

DETAILED DESCRIPTION OF THE PREFERRED EMBODIMENTS

Figures 1, 4:
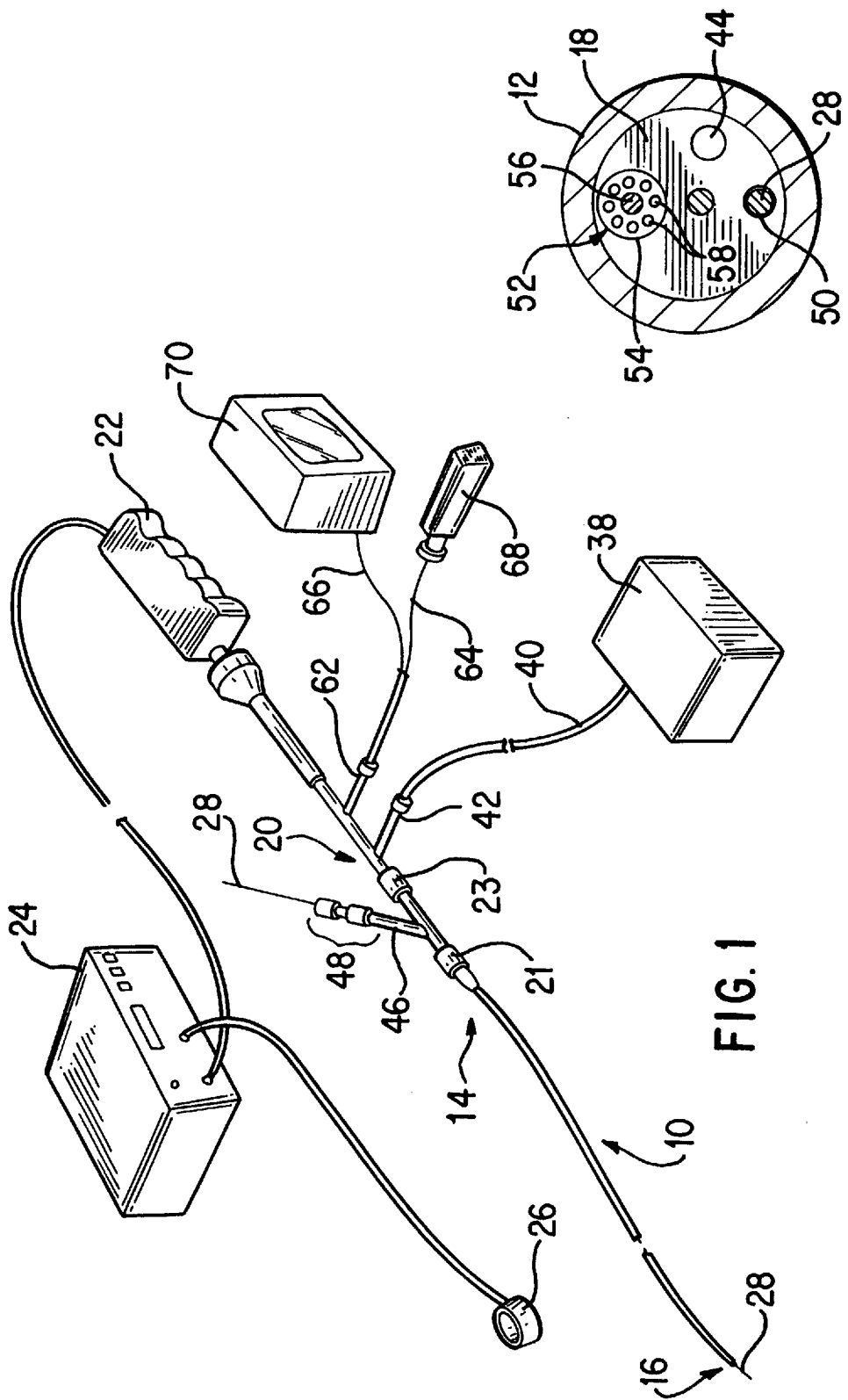
FIG. 1 is a perspective view of an ultrasound catheter system according to the present invention for use in effecting percutaneous revascularization of the myocardium.
FIG. 4 is a cross-sectional view through line 4—4 of FIG. 3.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

1. Percutaneous Myocardial Revascularization

FIGS. 1–4 illustrate an ultrasound system according to the present invention for use in percutaneous myocardial revascularization. The ultrasound system includes an ultrasonic catheter device 10 which has a deflectable elongate catheter body 12 having a proximal end 14, a distal end 16, and defining a lumen 18 extending longitudinally therethrough. The ultrasound catheter device 10 is operatively coupled, by way of a proximal connector assembly 20, to an ultrasound transducer 22. The ultrasound transducer 22 is connected to a signal generator 24. The signal generator 24 is provided with a foot actuated on-off switch 26. When the foot actuated on-off switch 26 is depressed, the signal generator 24 sends an electrical signal to the ultrasound transducer 22, which converts the electrical signal to ultrasonic energy. Such ultrasonic energy subsequently passes through the catheter device 10 of the present invention, thereby being delivered to the distal end 16 of the catheter body 12. A guidewire 28 may be utilized in conjunction with the catheter device 10, as will be more fully described below.

Figure 2:
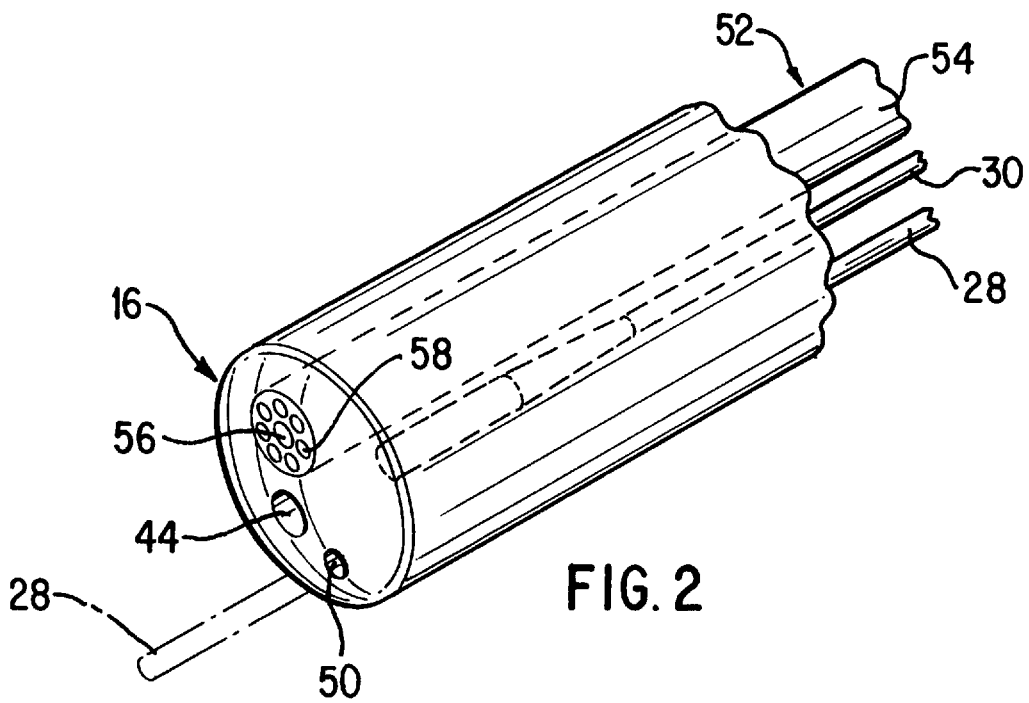
FIG. 2 is a partial enlarged perspective view of the distal end of an ultrasound catheter used with the system of FIG. 1.
Figure 3:
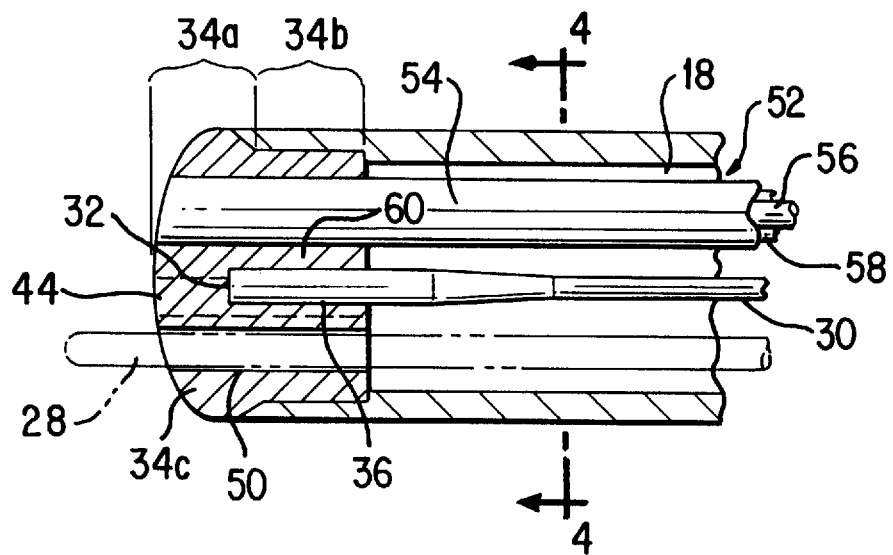
FIG. 3 is a longitudinal sectional view of the distal end of the catheter of FIG. 2.

The distal end 16 of the catheter body 12 of the catheter device 10 is shown, in detail, in FIGS. 2–4. In a preferred embodiment, the catheter body 12 is formed of a flexible plastic material such as nylon (Pebax ) manufactured by Atochimie, Cour be Voie, Hauts Ve-Sine, FRANCE. The flexible catheter body 12 is preferably in the form of an elongate tube having one or more lumens extending longitudinally therethrough. However, as previously explained, in the preferred embodiment of the present invention, only a single lumen 18 extends longitudinally through the tubular catheter body 12. Extending longitudinally through the lumen 18 of the catheter body 12 is an elongate ultrasound transmission member 30 or waveguide having a proximal end which is connectable to the ultrasound transducer 22 such that ultrasonic energy will pass through the ultrasound transmission member 30. As such, when the foot actuated on-off switch 26 operatively connected to the ultrasound transducer 22 is depressed, ultrasonic energy will pass through the ultrasound transmission member 30 to the distal end 32 thereof and, hence, the distal end 16 of the catheter body 12. More particularly, the ultrasound transmission member 30 serves to transmit the ultrasonic energy from the proximal connector assembly 20 to a distal head 34 mounted on the distal end 16 of the catheter body 12.

The distal head 34 has a substantially rigid member affixed to the distal end 16 of the catheter body 12. In the embodiment shown, the distal head 34 comprises a generally frusto-conical distal portion 34a, and a generally cylindrical proximal portion 34b. The proximal portion 34b of the distal head 34 is inserted into the open distal end 16 of the catheter body 12. The outer diameter of the proximal portion 34b of the distal head 34 is approximately the same as or slightly less than the inner diameter of the lumen 18 of the catheter body 12 such that the proximal portion 34b may be inserted into the distal end 16 of the catheter body 12 to a point whereat the distal portion 34a of the distal head 34 abuts the catheter body 12. Preferably, the outer diameter of the distal portion 34a is approximately the same as the outer diameter of the catheter body 12, thereby forming a generally smooth outer surface at the juncture of the distal head 34 and the catheter body 12, as shown in FIGS. 2 and 3.

The distal head 34 is firmly bonded, attached, or connected to the catheter body 12 such that the distal head 34 is prevented from undergoing longitudinal or transverse movements separate from or relative to the catheter body 12. Such affixation of the distal head 34 to the catheter body 12 increases the conveyance of ultrasound energy into the distal end 16 thereof. Such bonding connection or attachment of the distal head 34 to the catheter body 12 may be accomplished by any suitable manner. One manner of attaching the distal head 34 to the catheter body 12 is through the use of an adhesive which is applied to the outer surface of the proximal portion 34b of the distal head 34 prior to the insertion thereof into the distal end 16 of the catheter body 12. The adhesive may comprise any suitable adhesive, such as cyanoacrylate (e.g., Loctite Corp., Ontario, Canada or Aron Alpha , Borden, Inc., Columbus, Ohio) or polyurethane (e.g., Dymax , Dymax Engineering Adhesive, Torrington, Connecticut) to firmly bond and attach the distal head 34 to the catheter body 12.

The distal head 34 may be formed of any suitable rigid material, such as metal or plastic. The distal head 34 is preferably formed of radiodense material so as to be easily discernible by radiographic means. Accordingly, the distal head 34 may preferably be formed of metal or, alternatively, may be formed of plastic, ceramic, or rubber materials, optionally having one or more radiodense markers affixed thereto or formed therein. For example, the distal head 34 may be molded of plastic, such as acrylonitrile-butadine-styrene (ABS) and one or more metallic foil strips or other radiopaque markers may be affixed to such plastic distal head 34 in order to impart sufficient radiodensity to permit the distal head 34 to be readily located by radiographic means. Additionally, in embodiments wherein the distal head 34 is formed of molded plastic or other non-metallic material, a quantity of radiodense fillers, such as powdered Bismuth or Barium Sulfate ($BaSO_4$) may be disposed within the plastic or other nonmetallic material of which the distal head 34 is formed so as to impart enhanced radiodensity thereto.

In devices wherein the distal head 34 is formed of plastic, the surrounding catheter body 12 may be thoroughly welded, heat sealed, or solvent welded to the plastic distal head 34, in accordance with the types of plastics employed. As an alternative to the use of adhesives, various mechanical or frictional connectors, such as screw threads, lugs, or other surface modifications formed on the proximal portion 34b of the distal head 34, may be utilized to hold the distal head 34 in a fixed position relative to the distal end 16 of the catheter body 12. In such embodiments, corresponding grooves, detents, or surface modifications may also be formed in the surrounding innerluminal surface of the catheter body 12 so as to cooperate with any such threads, lugs, or other surface modifications formed on the opposing surface of the distal head 34. Such threads, lugs, or other surface modifications will be configured and constructed as to mechanically or frictionally hold the distal head 34 in fixed position relative to the catheter body 12.

As best seen in FIG. 3, the ultrasound transmission member 30 is inserted into a bore 36 which extends longitudinally into the proximal portion 34b of the distal head 34. The distal end 32 of the ultrasound transmission member 30 is then firmly held within the bore 36 by the frictional engagement thereof to the surrounding material of the distal head 34, or by other mechanical or chemical affixation means such as weldments, adhesive, etc. Firm affixation of the ultrasound transmission member 30 to the distal head 34 serves to facilitate direct transmission of the quanta of ultrasonic energy passing through the ultrasound transmission member 30 to the distal head 34. As a result, the distal head 34, and a distal portion of the tubular catheter body 12, are caused to undergo ultrasonic vibration in accordance with the combined quanta of ultrasonic energy being transmitted through the ultrasound transmission member 30.

In the preferred embodiment, the ultrasound transmission member 30 may be formed of any material capable of effectively transmitting the ultrasonic energy from the ultrasound transducer 22 to the distal head 34, including but not necessarily limited to metal, plastic, hard rubber, ceramic, and/or composites thereof. In accordance with one aspect of the invention, all or a portion of the ultrasound transmission member 30 may be formed of one or more materials which exhibit super-elasticity. Such materials should preferably exhibit super-elasticity consistently within the range of temperatures normally encountered by the ultrasound transmission member 30 during operation of the catheter device 10. Specifically, all or part of the ultrasound transmission member 30 may be formed of one or more metal alloys known as "shape member alloys".

Examples of super-elastic metal alloys which are usable to form the ultrasound transmission member 30 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 30 of the present invention operates, any and all of which super-elastic metal alloys may be usable to form the super-elastic ultrasound transmission member 30.

In particular, one presently preferred super-elastic metal alloy of which the ultrasound transmission member 30 may be formed is a nickel-titanium alloy wire made up of 55.8% nickel (NiTi containing 55.8% weight percent NiTi). Such material is commercially available as Tinel wire from Raychem Corporation, Menlo Park, California.

As seen from FIG. 3, the ultrasound transmission member 30 may be tapered, narrowed, or otherwise reduced in crosssectional dimension within the catheter device 10 so as to decrease the rigidity of the ultrasound transmission member 30 and/or to cause amplification of the ultrasound transmitted to and from the distal end 32 thereof. The distal end 32 of the ultrasound transmission member 30 received into the bore 36 is preferably enlarged from a narrowed shaft section to facilitate greater efficiency in the transmission of ultrasound energy from the ultrasound transmission member 30 to the distal head 34.

The proximal connector assembly 20 of the catheter device 10 comprises an elongate, rigid body defining frontal, mid and rear portions. The frontal portion of the body is firmly connected to the proximal end 14 of the catheter body 12 via a threaded gripping member 21 engaged thereto. In this respect, the proximal end 14 of the catheter body 12 preferably has a flared configuration and includes an annular flange formed on the outermost end thereof which is brought into sealed engagement with the proximal connector assembly 20 when the gripping member 21 is threadably engaged to the body. The proximal end of the frontal portion is connected to the distal end of the mid-portion of the body via a second gripping member 23. To facilitate the aforementioned construction, threads are formed on the distal ends of the frontal and mid-portions of the proximal connector assembly 20. The extreme proximal end of the rear portion of the proximal connector assembly 20 is provided with a sonic connector assembly or apparatus which is configured to effect operative attachment of the proximal end of the ultrasound transmission member 30 to the horn of the ultrasound transducer 22. A more thorough description of the manner and apparatus used to facilitate the operative attachment of the ultrasound transmission member 30 to the ultrasound transducer 22 is set forth in U.S. Pat. No. 5,312,328 to Nita et al., the entire disclosure of which is hereby expressly incorporated herein by reference.

In the present invention, an injection pump 38 is connected, by way of an infusion tube 40, to an infusion port or sidearm 42 in the mid-portion of the proximal connector assembly 20. The injection pump 38 is used to infuse coolant fluid (e.g., 0.9% NaCl solution) into and/or through the catheter device 10, and more particularly into the lumen 18 of the catheter body 12. Such flow of coolant fluid may be utilized to prevent overheating of the ultrasound transmission member 30 extending longitudinally through the lumen 18. Due to the desirability of infusing coolant fluid into the catheter body 12, extending longitudinally through the distal head 34 is at least one fluid outflow aperture 44 which permits the coolant fluid to flow from the lumen 18 out of the distal end 16 of the catheter body 12. Such flow of the coolant fluid through the lumen 18 serves to bathe the outer surface of the ultrasound transmission member 30, thereby providing for an equilibration of temperature between the coolant fluid and the matter of the ultrasound transmission member 30. Thus, the temperature and/or flow rate of coolant fluid may be adjusted to provide adequate cooling and/or other temperature control of the ultrasound transmission member 30.

In addition to infusing coolant fluid into and/or through the catheter device 10, the injection pump 38 may alternatively be utilized to infuse irrigation fluid into the lumen 18 of the catheter body 12 for purposes of removing debris from within the lumen of a vessel and/or forming a fluidic column to remove blood from the region of the distal head 34 and enhance the image transmitted by the endoscopic visualization apparatus incorporated into the catheter device 10 as will hereinafter be described.

In additon to the foregoing, the injection pump 38 may be utilized to infuse a radiographic contrast medium into the catheter device 10 for purposes of imaging. Examples of iodinated radiographic contrast media which may be selectively infused into the catheter device 10 via the injection pump 38 are commercially available as Angiovist 370 from Berlex Labs, Wayne, N.J. and Hexabrix from Malinkrodt, St. Louis, MO.

Formed on and extending outwardly from the frontal portion of the proximal connector assembly 20 is a guidewire insertion sidearm 46 for receiving the transluminal body guidewire 28. The guidewire insertion sidearm 46 includes a hollow bore extending therethrough which communicates with the bore of the proximal connector assembly 20. A guidewire gripping/sealing apparatus 48 may be mounted on the guidewire insertion sidearm 46 to grasp and hold the guidewire 28 in a fixed longitudinal position relative to the catheter device 10 and to provide a seal to prevent the backflow of blood through the catheter device 10. Examples of guidewire gripping/sealing apparatus 48 which may be utilized in this application include those which are available commercially as Product Nos. 1905017A and 1905014A from Medical Disposables International, West Conshocken, Pa.

The distal head 34 is provided with a guidewire passage aperture 50 which extends longitudinally therethrough. The guidewire passage aperture 50 is preferably formed through the distal head 34 at a location inboard of the catheter body 12 such that the guidewire 28 may pass therethrough into the lumen 18 of the catheter body 12. This embodiment of the catheter device 10 wherein the guidewire 28 passes through the guidewire passage aperture 50 and into the lumen 18 of the catheter body 12 constitutes an "over-the-wire" embodiment of the present invention. Additionally, the guidewire passage aperture 50 may be sized so as to be slightly larger than the outer diameter of the guidewire 28 to be passed therethrough so as to permit the coolant fluid infused into the lumen 18 to pass out of the guidewire passage aperture 50, even when the guidewire 28 is extending therethrough, in addition to the fluid outflow aperture 44. The catheter device 10 may, thus, be advanced and/or retracted over a pre-positioned guidewire in accordance with typical operative technique utilized in interventional cardiology procedures such as percutaneous transluminal angioplasty procedures. Those skilled in the art will appreciate that modifications, which are well-known in the art, can be made to the catheter body 12 to provide "monorail" (also known as "quick exchange") embodiments of the catheter device 10.

In addition to the ultrasound ablation apparatus as previously described, the catheter device 10 also incorporates an endoscopic visualization apparatus. In the preferred embodiment, the visualization apparatus comprises an elongate transmission member 52 extending longitudinally through the lumen 18 of the catheter body 12. The transmission member 52 comprises a tubular outer sheath 54 having at least one image transmitting optical fiber bundle 56 extending longitudinally therethrough. The image transmitting optical fiber bundle 56 is encircled by a multiplicity of light transmitting optical fiber bundles 58 of smaller diameter, which also extend longitudinally through the outer sheath 54. As such, both the image transmitting optical fiber bundle 56 and light transmitting optical fiber bundles 58 extend along the entire length of the transmission member 52 to the distal end thereof and are encased in the outer sheath 54 which serves to protect the integrity of the optical fiber bundles 56, 58.

As best seen in FIG. 3, the distal end of the transmission member 52 is inserted into a bore 60 which extends longitudinally through the distal head 34. The distal end of the transmission member 52 is firmly held within the bore 60 by frictional engagement to the surrounding material of the distal head 34, or by other mechanical or chemical affixation means. In this respect, the distal end of the transmission member 52 is preferably held within the bore 60 via the utilization of an adhesive which is applied to the distal region of the outer surface of the sheath 54 prior to the insertion of the transmission member 52 into the bore 60. Disposed on the distal end of the transmission member 52 is an optic lens which is a glass gradient index lens bonded to the distal ends of the image transmitting and light transmitting optical fiber bundles 56, 58 by an acrylic ester ultraviolet cured adhesive.

As best seen in FIG. 3, the lens preferably has an arcuate configuration such that when the distal end of the transmission member 52 is extended through and held firmly within the bore 60, the lens is substantially continuous with the arcuately contoured outer surface 34c of the distal portion 34a of the distal head 34. As such, when the transmission member 52 is properly engaged to the distal head 34, the light transmitting optical fiber bundles 58 are operable to transmit light from the proximal end of the transmission member 52 beyond the distal end 16 of the catheter device 10 to illuminate an object of interest. Additionally, the image transmitting optical fiber bundle 56 is able to transmit light received by the lens back to the proximal end of the transmission member 52. The image and light transmitting optical fiber bundles 56, 58 are preferably made of silica optical fibers, though other materials may alternatively be utilized.

In the present invention, the distal end of the transmission member 52 need not include a separate lens bonded thereto. In this respect, the distal end of the transmission member 52, and hence the distal ends of the image and light transmitting optical fiber bundles 56, 58, may be polished rather than having the lens bonded thereto. As will be recognized, when the distal end of the transmission member 30 is polished rather than having a lens affixed thereto, the transmission member 52 is cut in a manner wherein the polished distal end thereof will be substantially continuous with the arcuately contoured outer surface 34c of the distal portion 34a when the transmission member 52 is extended through and held firmly within the bore 60.

The proximal end of the transmission member 52 extends from a sidearm 62 formed on the mid-portion of the proximal connector assembly 20 and is preferably separated into two sections consisting of a first section 64 through which the light transmitting optical fiber bundles 58 are extended, and a second section 66 through which the image transmitting optical fiber bundle 56 is extended. The first section 64, and, hence, the proximal ends of the light transmitting optical fiber bundles 58, are operatively connected to a light source 68 which may be selectively activated to transmit light through the light transmitting optical fiber bundles 58 to the distal end of the transmission member 52. The second section 66, and, hence, the proximal end of the image transmitting optical fiber bundle 56, is operatively connected to an integrated camera and monitor apparatus 70 which allows an image from the distal end 16 of the catheter device 10 to be observed when the light source 68 is activated. However, it will be recognized that the camera and monitor may be provided as separate components which are operatively coupled to the image transmitting optical fiber bundle 56 at any location along the catheter device 10.

Due to the inclusion of the ultrasound transmission member 30 and the endoscopic transmission member 52, the catheter device 10, when advanced into a vessel or the heart, can be used to visually identify the internal structure of the vessel and the heart to facilitate proper positioning of the catheter device 10 for carrying out the procedure.

FIG. 5 illustrates the use of the ultrasound system of FIGS. 1–4 to effect percutaneous revascularization of the myocardium. The deflectable elongate catheter body 12 is inserted into the vasculature of a patient, generally through a major blood vessel (such as the femoral artery) or other organ affording access to an area of the heart 100 such as a ventricle 116 having an area 118 in need of increased blood circulation. A guidewire 28 may first be inserted into the patient's vasculature and guided to the area 118, and the catheter body 12 then passed over the guidewire 28 and guided to the area 118. Alternatively, the catheter body 12 may be placed inside a deflectable guiding catheter (not shown) for added degree of steerability and control. As the catheter body 12 is being inserted into the vessel, the light source 68 and camera/monitor apparatus 70 are preferably activated so as to transmit optical images from the distal end 16 of the catheter body 12 to the operator. The catheter body 12 is guided through the vasculature until the distal head 34 is adjacent the desired area 118 of revascularization.

After the distal head 34 has been properly positioned adjacent the area 118, the light source 68 and camera/monitor apparatus 70 are deactivated and the on-off switch 26 depressed thereby causing ultrasonic energy to be transmitted from the ultrasound transducer 22 to the distal head 34 via the ultrasound transmission member 30. In accordance with the present invention, the therapeutic ultrasound is preferably applied at frequencies ranging from 20 to 100 kHz, and can be operated in a either continuous wave mode or a pulse wave mode. The transmission of the ultrasonic energy through the ultrasound transmission member 30 causes the distal head 34 to vibrate, thereby producing a massaging effect on the desired area 118 which is in contact with the vibrating distal head 34. In some instances, the massaging effect alone is sufficient to improve blood circulation in the myocardium and the transmission of ultrasonic energy through the ultrasound transmission member 30 is stopped before any channels 120 are formed in the wall of the heart.

The use of ultrasound for muscle relaxation is already known. The application of ultrasound vibrations causes smooth muscles to relax, and vessels to expand (also known as vaso-relaxation). In addition, ultrasound has been shown to increase cardiac muscle contraction. In the present invention, this massaging concept is applied to improve blood circulation in the myocardium. When the wall of the heart 100 is massaged by the distal head 34, the distal head 34 does not cut or remove any tissue from the heart wall. Since the distal head 34 is blunt, the application of ultrasonic energy to the distal head 34 alone will not cut or remove tissue from the heart wall.

If the massaging effect alone is insufficient to improve blood circulation in the myocardium 124, the transmission of ultrasonic energy through the ultrasound transmission member 30 is continued. The physician can use the ultrasonic energy to scrape or cut small portions of tissue at the endocardium 122, as indicated at 125 in FIG. 6A, which may then be sufficient to improve blood circulation in the myocardium 124. Alternatively, the transmission of ultrasonic energy through the ultrasound transmission member 30 is continued and a channel 120 can be formed in the endocardium 122 and extend a desired distance through the myocardium 124, with or without perforating the exterior of the epicardium 126. This procedure can be repeated to form a number of such channels 120b (see FIG. 6A). After all desired channels 120 have been formed, the catheter body 12 is withdrawn from within the patient's vasculature.

The blunt distal head 34 can be used to scrape or cut small portions of tissue of the endocardium 122, or to form channels 120, by increasing the vibrations of the distal head 34. Alternatively, a sharp distal head 34b, as shown in FIG. 6B, can be operated at the normal operating frequencies to remove tissue or to form channels 120.

Thus, the ultrasound system of FIGS. 1–4 can be operated to effect myocardial revascularization in one of four ways. First, the distal head 34 can be used to massage the endocardium 122 at the area of interest without cutting or removing any tissue thereat. Second, the distal head 34 can be used to scrape or cut small portions of tissue of the endocardium 122. Third, channels 120 can be formed in the endocardium 122 and extend a desired distance through the myocardium 124, without perforating the exterior of the epicardium 126. Fourth, the channels 120 can extend through the myocardium 124 and perforate the exterior of the epicardium 126. If the epicardium 126 is perforated, then an incision must be made in the patient's chest to allow access to the epicardium 126 for the application of force to cause the epicardium 126 to seal itself.

During this procedure, the heart beat is preferably monitored, and ultrasound energy is preferably transmitted between heart beats (i.e., at heart rest). The application of ultrasound energy may be synchronized with EKG.

Although the ultrasound system has been described as including an endoscopic visualization apparatus for assisting the physician in viewing the positioning of the catheter body 12 and its distal head 34, it will be appreciated by those skilled in the art that the endoscopic visualization apparatus can be omitted. The positioning of the catheter body 12 may be viewed by fluoroscope imaging. It may also be desirable to add one or more radiopaque marker bands to the distal end 16 of the catheter body 12 for fluoroscopic imaging.

Although the ultrasound system has been described as constituting the elements described hereinabove, it will be appreciated by those skilled in the art that other ultrasound systems can be utilized for percutaneous myocardial revascularization without departing from the spirit and scope of the present invention. Non-limiting examples of such systems are illustrated in U.S. Pat. Nos. 5,304,115 (Pflueger et al.), 5,267,954 (Nita), whose disclosures are incorporated by reference as though fully set forth herein.

In addition, those skilled in the art will appreciate that it is possible to provide an ultrasound transducer adjacent or near the distal end of the catheter device 10 to obviate the need for an ultrasound delivery system, such as an ultrasound transmission member or wire. By eliminating the ultrasound transmission member, the catheter device can be provided with a lower profile and can be made more flexible, which can be useful for applications where the catheter device must navigate through tortuous vessels. FIGS. 7–8 illustrate two such examples.

FIG. 7 illustrates a distal section of a catheter device 300 having an outer tube 302 and an inner tube 304 disposed inside the lumen 310 of the outer tube 302. A distal head 306 is attached to the distal ends of the outer tube 302 and the inner tube 304. The distal head 306 has a distal portion 306a, a generally cylindrical central portion 306b, a generally cylindrical proximal portion 306c, and a thin neck portion 306d, which are progressively stepped so that the diameters of the distal portion 306a, the central portion 306b, the proximal portion 306c and the neck portion 306d decrease from the distal to the proximal direction. The distal portion 306a may be provided with a frusto-conical configuration similar to distal head 34 above, or it may be provided with a protruding or narrow tip 308 as shown in FIG. 7. The distal head 306 is preferably made from a material providing good acoustic properties, including but not limited to titanium, aluminum, stainless steel, porcelain, PVC and plastic.

The central portion 306b is inserted into the open distal end of the outer tube 302, and the proximal portion 306c is inserted into the open distal end of the inner tube 304. The outer diameter of the central portion 306b is approximately the same as or slightly less than the inner diameter of the lumen 310 of the outer tube 302 such that the central portion 306b may be inserted into the distal end of the outer tube 302 to a point whereat the distal portion 306a abuts the outer tube 302. Similarly, the outer diameter of the proximal portion 306c is approximately the same as or slightly less than the inner diameter of the lumen 312 of the inner tube 304 such that the proximal portion 306c may be inserted into the distal end of the inner tube 304 to a point whereat the central portion 306b abuts the inner tube 304. The distal head 306 may be firmly bonded, attached, or connected to the outer and inner tubes 302 and 304 at connection points 303 and 305, respectively, according to the methods described above for attaching distal head 34 to the catheter body 12. Irrigation channels 314 are provided in the distal head 306 and communicate with the lumen 310 of the outer tube 302 for carrying aspirating and/or cooling fluid to the distal head 306. The cooling fluid is used to reduce the heat build-up at the distal head 306 caused by the transducer, which is described in greater detail below.

A transducer is coupled to the neck portion 306d of the distal head 306 inside the lumen 312 of the inner tube 304. In this embodiment of the present invention, the transducer has a piezoelectric crystal cylinder 322 that is provided about the neck portion 306d and abutting the proximal portion 306c. A threaded tension screw 323 is secured to threads (not shown) provided in a threaded bore in the neck portion 306d to secure the cylinder 322 to the distal head 306. Electrodes 324 and 326 are provided at opposing ends of the cylinder 322, and the electrodes 324 and 326 are coupled to a power source via electrical leads 328 and 330, respectively. The electrodes 324 and 326, as well as the power source, may be of conventional design suitable for applying a voltage between the electrodes 324 and 326 in order to cause the mechanical generation of ultrasonic waves that will propagate along the longitudinal axis LA of the transducer. The piezoelectric crystal may be of any suitable material well known in the art having piezoelectric characteristics such as lead zircomate titanate (PZT). When a voltage is applied between the electrodes 324 and 326, the crystal cylinder 322 will contract and expand to cause the distal head 306 to vibrate longitudinally. The longitudinal vibrations from the transducer are amplified by the narrowed tip 308 and applied to the heart wall to revascularize the myocardium according to the methods described above in connection with the ultrasound system of FIGS. 1–4.

FIGS. 8A and 8B illustrate a distal section of another catheter device 400 having a catheter body 402 defining a single lumen 404. A distal head 406 is connected to the distal end 408 of the catheter body 402 via a wound coil 410. The coil 410 is preferably made from a material having good stress-strain properties, and being able to resist high temperatures. Such materials include, but are not limited to, metals, preferably a nickel-titanium alloy, and stainless steel. The distal head 406 has a distal portion 406a and a generally cylindrical proximal portion 406b, with the outer diameter of the proximal portion 406b being smaller than the outer diameter of the distal portion 406a. The distal portion 406a may be provided with a rounded and blunt configuration, as shown in FIG. 8.

The distal portion of the coil 410 is wrapped around and attached to the outer surface of the proximal portion 306b at location point 426 by welding, frictional engagement, binding, crimping, and other conventional methods. The proximal end 412 of the coil 410 is attached to the distal end 408 of the catheter body 402 by welding, epoxy, adhesives, frictional engagement, binding, crimping, and other conventional methods. In the preferred embodiment, the distal head 406 is not positioned inside the lumen 404 of the catheter body 402, but is supported by the coil 410 adjacent the distal end 408 of the catheter body 402. This construction provides the catheter device 400 with a flexible distal end.

The proximal portion 406b of the distal head 406 is provided with an annular bore 416 which is defined by an inner core 418 and the outer walls 420 of the proximal portion 406b. The bore 416 receives two half-cylindrical piezoelectric crystal pieces 422 and 424. The crystal pieces 422 and 424 may be made of the same material as crystal cylinder 322. The crystal pieces 422 and 424 are attached to the bore 416 by heat-conductive expoxy or other conventional mechanical trappings. Electrodes 430 and 432 are provided at opposing upper and lower edges of the crystal piece 422 at the proximal end of the crystal piece 422, and the electrodes 430 and 432 are coupled to a power source via electrical leads 434 and 436, respectively. Similarly, electrodes 440 and 442 are provided at opposing upper and lower edges of the crystal piece 424 at the proximal end of the crystal piece 424, and the electrodes 440 and 442 are coupled to a power source via electrical leads 444 and 446, respectively. The electrodes 430, 432, 440 and 442, as well as the power source, may be of conventional design suitable for applying a voltage between the electrode pairs 430, 432 and 440, 442 in order to cause the mechanical generation of ultrasonic waves that will cause the crystal pieces 422 and 424 to expand and contract in a transverse manner. This results in axial expansion and contraction of crystal pieces 422 and 424, which will create energy which is transferred to the distal portion 406a of the distal head 406. The energy at distal portion 406a is applied to the heart wall to revascularize the myocardium according to the methods described above in connection with the ultrasound system of FIGS. 1–4, except that the catheter device 400 cannot be used to provide a massaging effect alone. The coil 410 operates to prevent the temperature build-up or heat from being transferred to the catheter body 402, thereby protecting the catheter body 402 from damage.

In addition to the embodiments disclosed in FIGS. 8–9, non-limiting examples are also illustrated in U.S. Pat. Nos. 5,318,014 (Carter) and 5,431,663 (Carter), whose disclosures are incorporated by reference as though fully set forth herein.

2. Intra-Operative Myocardial Revascularization

FIG. 9 illustrates an ultrasound device 150 for use in effecting intra-operative revascularization of the myocardium. The ultrasound device 150 includes three primary components, a distal tip 152, an ultrasound probe 154 and an ultrasound transducer 156. The three components may be provided integrally in one piece, or can be provided separately and connected to each other by means of threads or other suitable attachment mechanisms.

In a preferred embodiment, the distal portion of the transducer 156 is provided with threads for threadably coupling threads provided at the proximal portion of the probe 154. The distal tip 152 is affixed to the distal portion of the probe 154 by any of the methods described above for affixing the distal head 34 to the catheter body 12. In addition, the distal tip 152 may be made from any of the materials described above for the distal head 34.

The transducer 156 may be similar to the transducer 22 in FIG. 1. The transducer 156 is likewise connected to a signal generator 24 which may be actuated to send an electrical signal to the transducer 156. The transducer 156 then converts the electrical signal to ultrasonic energy, which is subsequently passed through the probe 154 to be delivered to the distal section 152. The probe 154 may be made from a material having good acoustic and good stress-strain characteristics, and is preferably made from aluminum or titanium.

FIGS. 10A to 10E illustrate various configurations for the distal tip 152. The distal tip 152a in FIG. 10A has a smooth, rounded and blunt configuration. The distal tip 152b in FIG. 10B has a bulbous configuration with a sharp tip 160. The distal tip 152c in FIG. 10C has two flat side surfaces 162, a curved or tapered top edge 164 and a curved or tapered bottom edge 166. The top and bottom edges 164 and 166 curve or taper towards a sharp tip 168. The distal tip 152d in FIG. 10D is configured as a scalpel having a flat top edge 170, with a cutting edge or blade 172 extending from the top edge 170 downwardly and inwardly. The distal tip 152e in FIG. 10E has a conical configuration with two edges 174 and 176 tapering towards a sharp tip 178.

Figure 11:
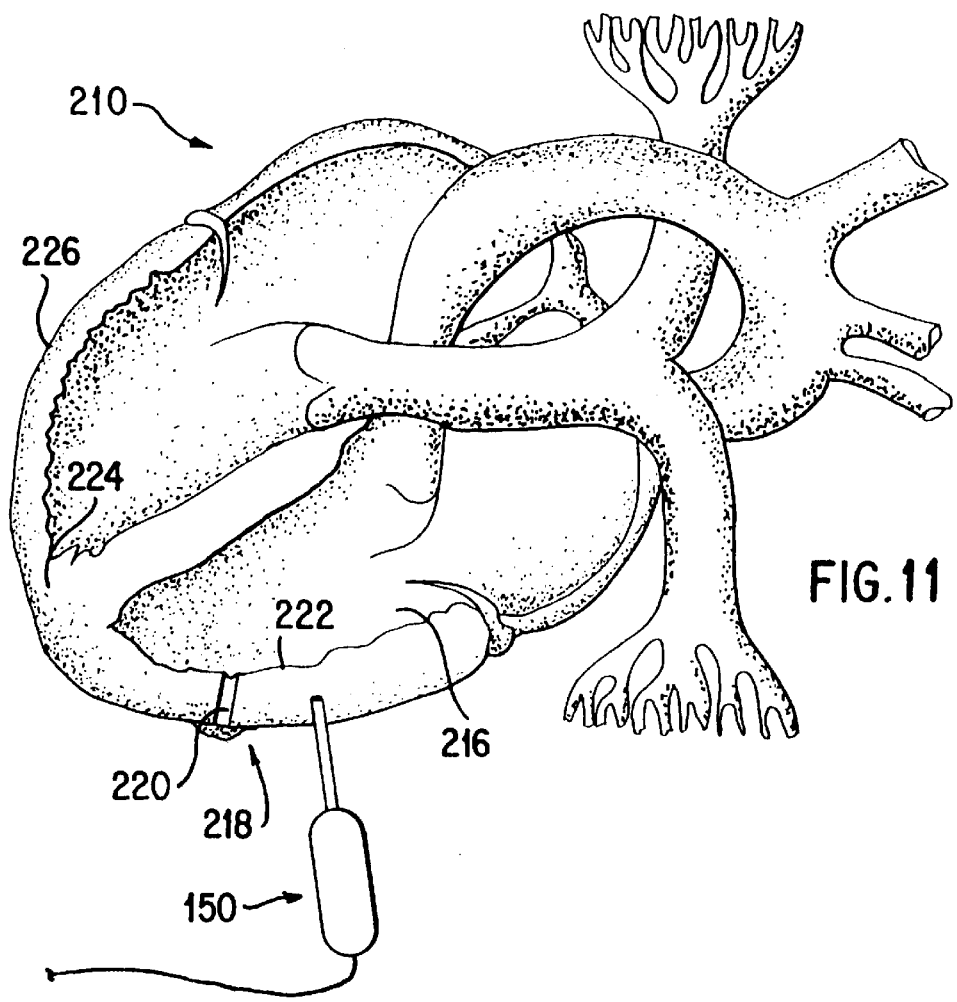
FIG. 11 is a schematic section of a human heart showing intra-operative revascularization of the myocardium according to the present invention.
Figure 12:
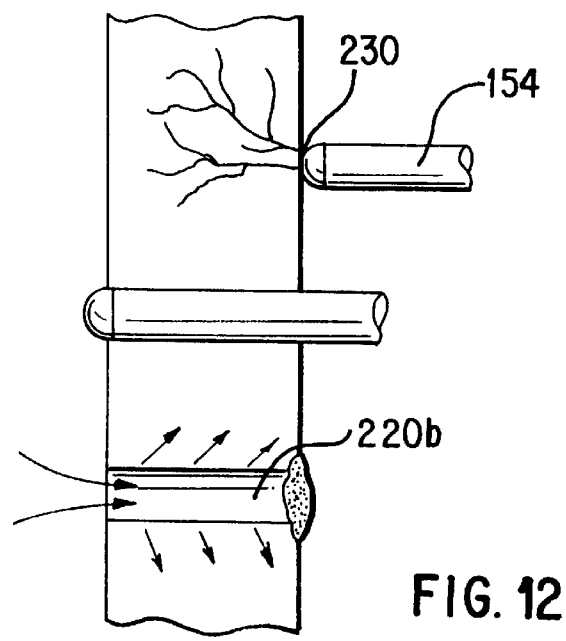
FIG. 12 is a schematic sectional view of channels created by intra-operative revascularization of the myocardium according to the present invention.

FIG. 11 illustrates the use of the ultrasound system of FIG. 9 present invention to effect intra-operative revascularization of the myocardium. The ultrasound device 150 is inserted into the chest cavity. This insertion may require only a small incision, which would minimize the invasiveness of the procedure. The distal tip 152 is then placed adjacent an area such as ventricle 216 having an area 218 in need of increased blood circulation. After the distal tip 152 has been properly positioned adjacent the area 218, the ultrasound transducer 156 is actuated to transmit ultrasonic energy to the distal tip 152 via the probe 154, causing distal tip 152 to vibrate, thereby producing a massaging effect on the desired area 218 which is in contact with the vibrating distal tip 152. In some instances, the massaging effect alone is sufficient to improve blood circulation in the myocardium and the transmission of ultrasonic energy is stopped before any tissue is cut or removed from the epicardium 226. For example, see the location indicated by the numeral 230 in FIG. 12.

If the massaging effect alone is insufficient to improve blood circulation in the myocardium, the transmission of increased ultrasonic energy is continued and a channel 220 can be formed from the epicardium 226, and extend through the myocardium 224 and perforating the endocardium 222. Once the channel 220 has been formed, the portion of the channel 220 opening through the epicardium 226 is temporarily covered while a portion of the channel 220 extending through the epicardium 226 seals itself. This procedure can be repeated to form a number of such channels 220b (see FIG. 12). After all desired channels 220 have been formed, the ultrasound device 150 is withdrawn from the patient's chest cavity and the incision is sealed.

Any of the distal tips 152a–152e illustrated in FIGS. 10A–10E can be used. However, it is preferable to use a blunt tip, such as distal tip 152a, for providing the massaging effect only, since the other distal tips 152b–152e have sharp edges that will tend to cut or remove tissue from the epicardium 226.

In contrast with the method of effecting percutaneous myocardial revascularization according to the present invention, which presents four different methods, intra-operative myocardial revascularization according to the present invention presents only two ways. First, the distal tip 152 can be used to massage the epicardium 226 at the area of interest without cutting or removing any tissue thereat. Second, channels 220 can be formed through the myocardium 124 and perforate the endocardium 222.

During this procedure, the heart beat is preferably monitored, and ultrasound energy is preferably transmitted between heart beats (i.e., at heart rest). Again, the application of ultrasound energy may also be synchronized with EKG.

Those skilled in the art will appreciate that the sizes of the channels 120 and 220 formed in the heart wall can be varied by providing the distal head 34 or distal tip 152 with different shapes and sizes.

Thus, the present invention provides ultrasound devices and methods that can be used to revascularize the myocardium using minimally-invasive procedures. Ultrasonic energy provides benefits not realized by the use of laser energy or other known means. For example, the ultrasound devices according to the present invention provide the physician with the option of not cutting or removing any tissue from the wall of the heart if massaging of the heart tissue is sufficient to revascularize the myocardium. The ultrasound devices according to the present invention further provide the physician with the option of forming channels of different depths and sizes, thereby allowing the physician to adapt the procedure to different cardiovascular conditions. In addition, ultrasonic energy is less harmful and traumatic to the heart than laser energy.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method of improving the circulation of blood to the muscle of the heart of a patient, comprising the steps of:
   (a) inserting a guidable elongated flexible ultrasound device into a patient's vasculature, the ultrasound device having a blunt distal head;
   (b) guiding the blunt distal head a distal end of the ultrasound device to an area of interest within the patient's heart to which increased blood flow is desired; and
   (c) applying ultrasonic energy via the blunt distal head to healthy tissue at the area of interest.

2. The method of claim 1, wherein step (c) further comprises the step of massaging the area of interest without cutting any portion of the heart wall at the area of interest.

3. The method of claim 2, wherein step (c) further comprises the step of removing some tissue from the area of interest.

4. The method of claim 2, wherein step (c) further comprises the step of forming a channel in the heart wall at the area of interest without perforating the epicardium of the heart wall at the area of interest.

5. The method of claim 2, wherein the ultrasound device comprises a blunt distal head positioned at its distal end.

6. The method of claim 1, wherein step (c) further comprises the step of forming a channel in the heart wall at the area of interest without perforating the epicardium of the heart wall at the area of interest.

7. The method of claim 6, wherein the distal end of the ultrasound device comprises a sharp edge.

8. The method of claim 1, wherein step (c) further comprises the step of forming a channel in the heart wall at the area of interest through the epicardium of the heart wall at the area of interest.

9. The method of claim 1, wherein step (c) is performed between heart beats.

10. The method of claim 1, further including the step of guiding the ultrasound device through a deflectable guiding catheter.

11. The method of claim 1, wherein step (b) further comprises the steps of inserting a guidewire into the patient's vasculature and passing the ultrasound device over the guidewire.

12. The method of claim 1, further comprising the step of providing the ultrasound device with an endoscopic visualization apparatus.

13. The method of claim 12, further comprising the step of visualizing the area of interest.

14. The method of claim 1, further including the step of providing an ultrasound transducer adjacent the distal end of the ultrasound device.

15. The method of claim 1, wherein step (c) further comprises the step of generating energy and vibrations at the distal end of the ultrasound device.

16. A method of improving the circulation of blood to the muscle of the heart of a patient, comprising the steps of:
   (a) directing a distal end of an ultrasound device into a patient's chest cavity;
   (b) guiding the blunt distal head of the ultrasound device within the patient's chest cavity to engage an exterior area of interest of the patient's heart in which increased blood flow is desired; and
   (c) applying ultrasonic energy via the blunt distal head to healthy tissue of the area of interest.

17. The method of claim 16, wherein step (c) further comprises the step of massaging the area of interest without cutting any portion of the exterior of the heart at the area of interest.

18. The method of claim 17, wherein step (c) further comprises the step of forming a channel in the heart wall at the area of interest.

19. The method of claim 17, wherein the distal end of the ultrasound device comprises a blunt distal tip.

20. The method of claim 16, wherein step (c) further comprises the step of forming a channel in the heart wall at the area of interest.

21. The method of claim 19, wherein the distal end of the ultrasound device comprises a sharp edge.

22. The method of claim 16, wherein step (c) is performed between heart beats.

* * * * *